United States Patent [19]

Yabe

[11] Patent Number: 4,654,701

[45] Date of Patent: Mar. 31, 1987

[54] BIOPSY INFORMATION RECORDING APPARATUS FOR ENDOSCOPE

[75] Inventor: Hisao Yabe, Tokyo, Japan

[73] Assignee: Olympus Optical Co., Ltd., Tokyo, Japan

[21] Appl. No.: 771,050

[22] Filed: Aug. 30, 1985

[30] Foreign Application Priority Data

Sep. 3, 1984 [JP] Japan .................................. 59-184153

[51] Int. Cl.⁴ .............................................. A61B 1/04
[52] U.S. Cl. ......................................... 358/98; 128/4;
128/749; 358/183
[58] Field of Search .......................... 358/98, 107, 183;
128/4–6, 749, 751

[56] References Cited

U.S. PATENT DOCUMENTS

| | | | |
|---|---|---|---|
| 3,924,608 | 12/1975 | Mitsui | 128/751 |
| 3,945,371 | 3/1976 | Adelman | 128/749 |
| 4,043,323 | 8/1977 | Komiya | 128/7 |
| 4,208,675 | 6/1980 | Bajon | 358/107 |
| 4,262,306 | 4/1981 | Renner | 358/107 |
| 4,573,450 | 3/1986 | Arakawa | 358/98 |

FOREIGN PATENT DOCUMENTS 373112 7/1939 Italy ..................................... 128/751

Primary Examiner—Howard W. Britton

[57] ABSTRACT

A biopsy information recording apparatus is disclosed which comprises a memory for storing, as a still picture frame, image information from an endoscopic image sensor provided in an endoscope, an input unit for providing information of a position at which biopsy material is extracted by forceps inserted into the forceps channel of the endoscope, and a counter for counting the number of biopsy extractions to provide information of the sampled order of the extracted biopsy material, the sampled order information being stored in a frame memory together with image information at a memory position corresponding to the position information.

5 Claims, 5 Drawing Figures

BIOPSY INFORMATION RECORDING APPARATUS FOR ENDOSCOPE

BACKGROUND OF THE INVENTION

This invention relates to a biopsy information recording apparatus for recording information concerning biopsy material extracted by endoscope forceps.

Heretofore, it has been the practice to extract biopsy material from a somatic cavity using forceps inserted into the forceps channel of an endoscope, and then to make an endoscopic diagnosis through examination of the extracted biopsy material. The operator, i.e., doctor, memorizes the extraction position and sequence number of biopsy material every time material is extracted, and writes the memorized positions and numbers in a patient's chart. If, however, the number of extraction positions or diseased parts is great, the extraction positions and sequence numbers are liable to be forgotton. This being the case, the one-to-one correspondence between the samples and the extraction positions is lost, thus obviating accurate diagnosis.

SUMMARY OF THE INVENTION

An object of the invention is to provide a biopsy information recording apparatus for an endoscope which permits easy and accurate recording of the extraction position and the sequence of extraction every time biopsy material is extracted.

According to the invention, there is provided a biopsy information recording apparatus which comprises a first memory for storing, as a still picture frame, image information from an endoscopic image pick-up unit provided in an endoscope; an input section inputting information of a position from which biopsy material is extracted by forceps inserted into the forceps channel of the endoscope, an output section for producing information of the sampled order of the extracted biopsy material, a second memory for storing the position information and sampled order information, and a section for recording the sampled order information in the first memory at a position corresponding to the position information.

DETAILED DESCRIPTION OF THE PREFERRED EMBODIMENT

Figure 1:
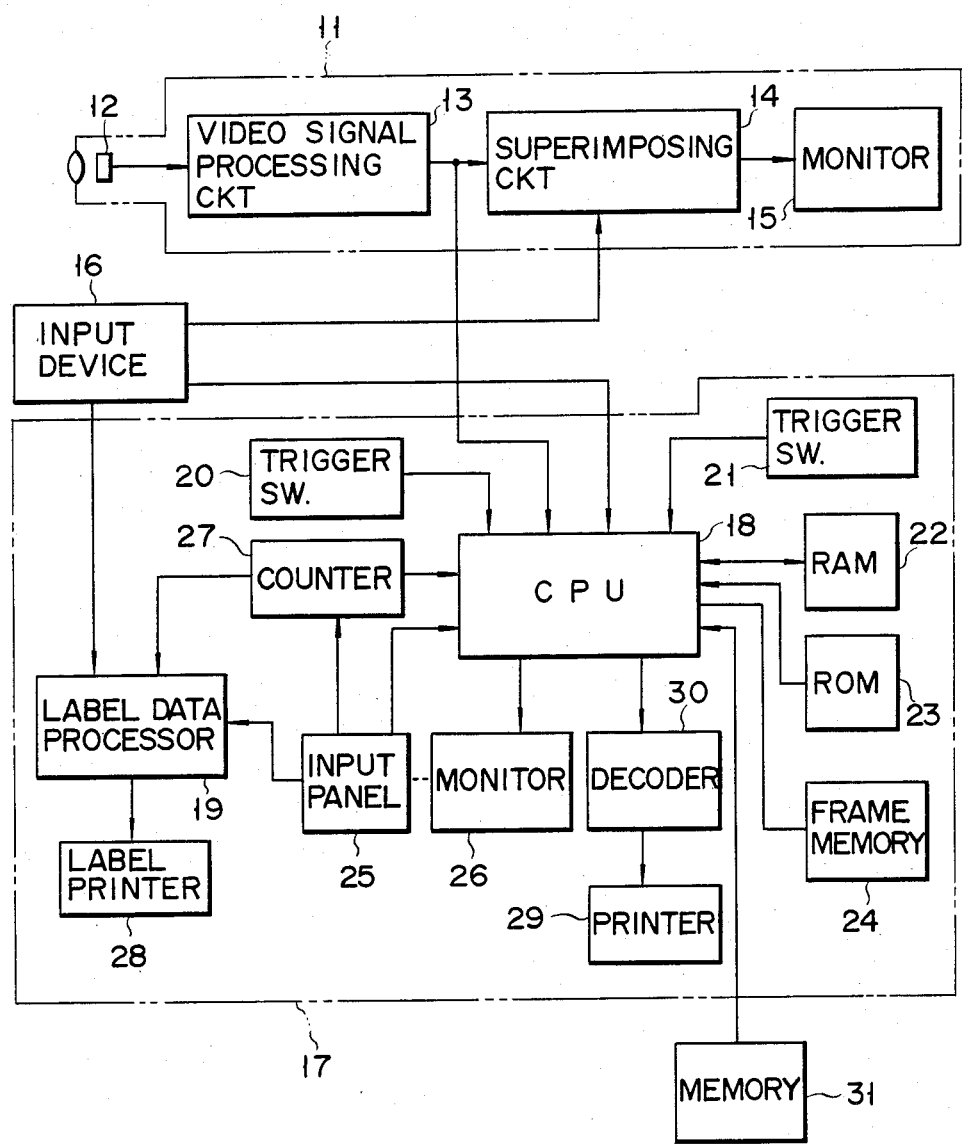
FIG. 1 is a block diagram showing an endoscopic system incorporating an embodiment of the biopsy information recording apparatus for endoscope according to the invention.

Referring to the block diagram of FIG. 1, an endoscope 11 includes a solid state image sensor, e.g., a CCD 12. The CCD 12 is connected to a video signal processing circuit 13, the output of which is coupled through a superimposing circuit 14 to a monitor 15.

An input device 16 is provided for inputting patient data such as a predetermined examination serial number, patient's name, patient's number, etc., prior to the endoscope examination. The output of the input device 16 is fed to the superimposing circuit 14 and also to a CPU 18 and a label data processor 19 in a data processing/printing section 17. A biopsy trigger switch 20, a printer trigger switch 21, a RAM 22, a ROM 23 and a frame memory 24 are connected to the CPU 18.

A data input panel 25 includes a touch panel provided integrally on the surface of a monitor 26. Biopsy data of an endoscope image is displayed on the monitor 26. When the touch panel 25 is touched, data corresponding to the touched position is provided. The output of the data input panel 25 is coupled to the CPU 18, label data processor 19 and counter 27. The output of the label data processor 19 is coupled to the label printer 28. A printer 29 is provided for printing an image, and it is connected to the CPU 18 through a decoder 30. Further, an external memory 31 is connected to the CPU 18.

Figure 2:
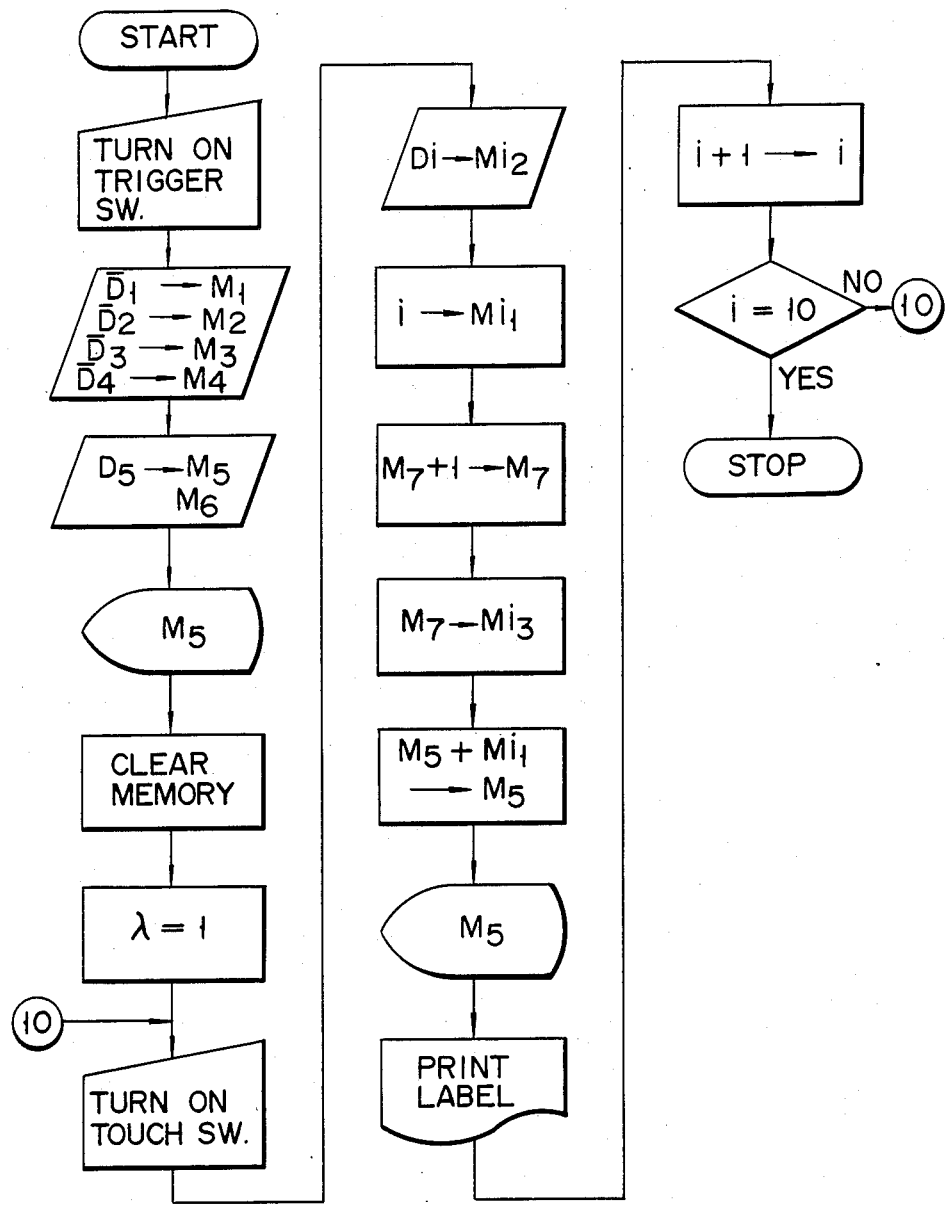
FIG. 2 is a flow chart explaining the operation of the biopsy information recording apparatus shown in FIG. 1.

The operation of the circuit of FIG. 1 will be explained with reference to the flow chart shown in FIG. 2.

When an endoscope takes a picture of the interior of a cavity upon being inserted into the cavity, a video signal from the CCD 12 is processed in the video signal processing circuit 13, and the output thereof is fed through the superimposing circuit 14 to the monitor 15. The image of the somatic cavity's interior is thus displayed on the monitor 15. When a somatic cavity portion, the biopsy material of which is thought to be necessary, is displayed, the operator observing the display on the monitor 15 produces a start command, provided through operation of the trigger switch 20. The trigger switch 20 thus produces a trigger signal to render the CPU 18 operative. At this time, the examination serial number (data D1), patient's name (data D2), patient's number (data D3) and examination date (data D4) are keyed in or read out of a card in the input device 16 and stored in respective memory areas M1 to M4 of the RAM 22. Then, the video signal processing circuit 13 digitally processes an image signal for one frame, and the resultant data is stored in memory areas M5 and M6 of the frame memory 24. The frame image data stored in the memory area M5 is displayed as a still picture on the monitor 26.

Then, memory areas where the biopsy sampled order data, biopsy position data and biopsy serial number data are stored, e.g., memory areas Mi1, Mi2 and Mi3 (i being 1 to 9), are cleared. Then, an initial value $\lambda=1$ is stored. When the input panel (i.e., touch panel) 25 is touched at a position corresponding to a position from which biopsy material is extracted by the forceps inserted into the forceps channel (not shown) of the endoscope 11, position data Di (i being 1 to 9) corresponding to the touched position is provided and stored in a memory area M12, for instance, of the RAM 22. The counter 27 is then incremented by 1 by a signal from the input panel 25, and the resultant count, which is "1" at this time, is stored in a memory area M11 of the RAM 22 as biopsy sampled order data. The biopsy serial number data relating to all patients stored in the external memory 31 are then stored in the memory area M7 of the RAM 22.

In a subsequent step, the content of the memory area M7 is updated with the addition of 1 to the biopsy serial number data. The lower 5 bits of the updated biopsy serial number data are then stored in a memory area Mi3. Thereafter, the biopsy simpled order data is superimposed on the frame image data in the memory area M5 of the frame memory 24, and the result is stored in the memory area M5. The image data in the memory area M5 is displayed on the monitor 26. At this time, the biopsy sampled order, i.e., "1", is displayed on the monitor 26 at the biopsy position.

Figure 3:
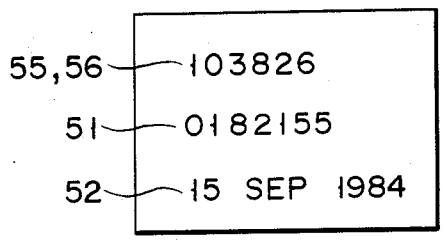
FIG. 3 is a view showing a label printed in the biopsy information recording apparatus shown in FIG. 1.

The label data processor 19 feeds the data of the input device 16, counter 27 and input panel 25, i.e., data corresponding to data stored in the memory areas Mi1, Mi3, M1 and M4 of the RAM 22, and representing the biopsy serial number, biopsy sampled order and examination date, to the label printer 28. The label printer 26 prints out a label as shown in FIG. 3. The biopsy sampled order is printed at the head of the 5 bits of the biopsy serial number. The back surface of the label is adhesive so that the label can be adhered to a sample tube which is to contain the extracted material as a biopsy sample for examination.

Subsequently, i is updated by the addition of 1. Then, a check is done as to whether i=10. In the event the judgement is NO, the routine returns to the step of touching the input panel.

When the next biopsy position data is input through the input panel 25, a biopsy sampled order "2" is displayed on the monitor 26 at a position corresponding to the position of the position of the endoscope after the sequence of operations described above is performed. When 10 biopsy samples are extracted in the above manner, it is detected that i=10, thus bringing to an end the printing process.

Figure 4:
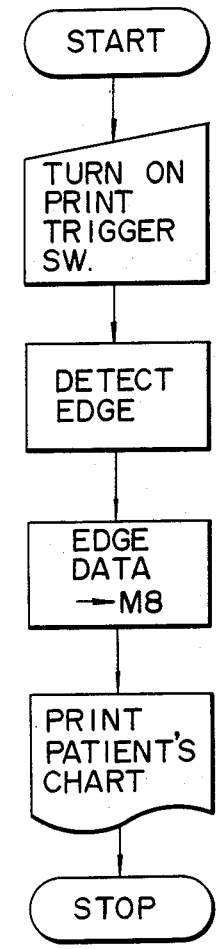
FIG. 4 is a flow chart illustrating a patient's chart print operation.

An interrupt program for printing out a patient's chart will now be described with reference to the flow chart of FIG. 4.

When the print trigger switch 21 is turned on, edge detection is done on the frame image in the memory area M6 of the frame memory 24. At this time, the print image position is shifted slightly, and the difference between the shifted and original image positions is noted. That is, a process similar to a differential calculation is executed. The detected edge, i.e., profile of the image, is converted to binary data. The resultant binary image, i.e., monochromatic image, is stored in the binary memory area M8 of the frame memory 24.

Figure 5:
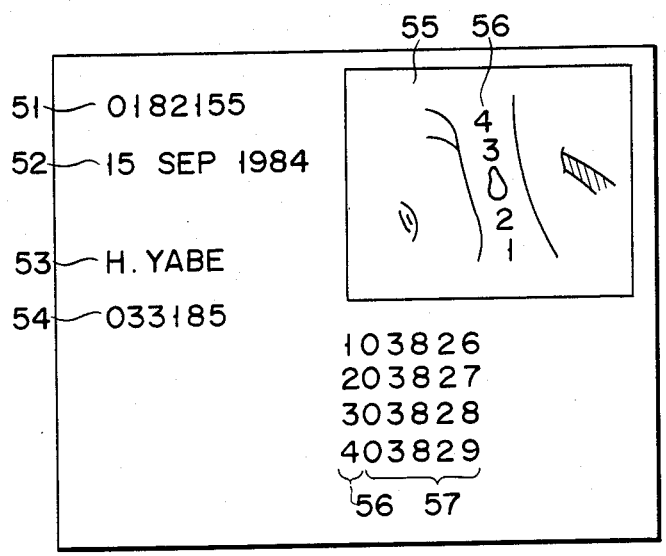
FIG. 5 is a view showing a printed patient's chart.

The binary image data in the binary memory area M8 is then read out and fed, along with data stored in the memory areas M1 to M4, Mi1 and Mi3, through the decoder 30 to the printer 29, so that a patient's chart, as shown in FIG. 5, is printed out. In the patient's chart illustrated, the biopsy serial number 51, biopsy extraction date 52, patient's name 53 and patient's number 54 are printed on the left side. On the right side, the endoscopic profile image 55 is printed. The profile image 55 contains biopsy sampled order (56) at positions corresponding to the extraction positions. The numbers of the biopsy sampled order (56) are printed below the profile image 55 in addition to the head of the biopsy serial number 58. The remaining space in the patient's chart is provided for the doctor to write the results of the examination or the like.

The initial value of the biopsy serial number may be changed by changing the data in the memory area M7. In this case, the initial data may be coupled from the input device 16 or other input devices.

As has been described in the foregoing, according to the invention, the biopsy position data and biopsy sampled order data are input every time an biopsy sample is extracted. Thus, even in the case where a large number of biopsy samples are extracted, the biopsy position data and biopsy sampled order data can be accurately and reliably stored without error, eliminating the possibility of mistaking either the position or the sequence of biopsy samples.

What is claimed is:

1. A biopsy information recording apparatus comprising:
   first memory means for storing, as a still picture frame, image information from an endoscopic image pick-up unit provided in an endoscope having a forceps channel;
   input means for inputting information representing a position at which biopsy material is extracted by forceps inserted into the forceps channel of said endoscope;
   means for producing information representing a sampled order of the extracted biopsy material;
   second memory means for storing said position information and sampled order information; and
   means for recording said sampled order information at the memory position of said first memory which corresponds to said position information.

2. The biopsy information recording apparatus according to claim 1, wherein said input means comprises:
   display means having a display surface for displaying the image information stored in said first memory means as a still picture frame; and
   touch switch panel means provided integrally on the display surface of said display means, and rendered operative when touched, thus providing positional information representing a given position of the still picture displayed on said display surface.

3. The biopsy information recording apparatus according to claim 1, wherein said input means comprises display means having a display surface for displaying, as a still picture frame, image information stored in said first memory means, and touch switch panel means provided integrally on the display surface of said display means and rendered operative when touched, thus providing positional information representative of a given position of the still picture displayed on said display surface; and wherein said sampled order information providing means counts an output signal from said touch switch panel means and providing sampled order information to said second memory means.

4. The biopsy information recording apparatus according to claim 2, wherein said display means displays both said sampled order information stored in said second memory means and said still picture information.

5. A biopsy information recording apparatus comprising:
   first memory means for storing, as a still picture frame, image information from an endoscopic image pick-up unit provided in an endoscope having a forceps channel;
   input means for inputting information of biopsy material extracted by forceps inserted into the forceps channel of said endoscope;
   second memory means for storing said position information and sampled order information;
   means for storing said sample order information at the memory position of said first memory means, which corresponds to said position information; and
   means for producing a patient's chart by printing said sampled order information and still picture information stored in said first memory means.

* * * * *